(12) United States Patent
Eden

(10) Patent No.: US 7,719,292 B2
(45) Date of Patent: May 18, 2010

(54) METHOD AND APPARATUS FOR ELECTROCHEMICAL CORROSION MONITORING

(75) Inventor: David A. Eden, Spring, TX (US)

(73) Assignee: Honeywell International Inc., Morristown, NJ (US)

( * ) Notice: Subject to any disclaimer, the term of this patent is extended or adjusted under 35 U.S.C. 154(b) by 264 days.

(21) Appl. No.: 11/974,251

(22) Filed: Oct. 12, 2007

(65) Prior Publication Data

US 2009/0096471 A1 Apr. 16, 2009

(51) Int. Cl.
*G01N 17/04* (2006.01)
*G01R 27/08* (2006.01)
(52) U.S. Cl. .................... 324/700; 324/71.2; 205/775.5
(58) Field of Classification Search .................. 324/700, 324/71.2; 205/775.5
See application file for complete search history.

(56) References Cited

U.S. PATENT DOCUMENTS

| | | | |
|---|---|---|---|
| 4,658,365 A | 4/1987 | Syrett et al. | |
| 5,006,786 A * | 4/1991 | McKubre et al. | 205/775.5 |
| 6,015,484 A | 1/2000 | Martincheck et al. | |
| 6,280,603 B1 | 8/2001 | Jovancicevic | |
| 6,320,395 B1 | 11/2001 | Bosch | |
| 6,797,149 B2 * | 9/2004 | Eden | 205/775.5 |
| 2004/0149594 A1 | 8/2004 | Eden | |

FOREIGN PATENT DOCUMENTS

WO WO 03/106976 A1 12/2003

OTHER PUBLICATIONS

Bosch et al., Instantaneous Corrosion Rate Measurement with Small-Amplitude Potential Intermodulation Techniques, Corrosion Science, Mar. 1996, vol. 52, pp. 204-212.
Meszaros et al., Study of the Rate of Corrosion of Metals by a Faradaic Distortion Method, III, Acta Chimica Academiac Scientiarum Hungaricae, Tomus 105, 1980, pp. 1-17.
Rao et al., AC Techniques to Evaluate the Kinetics of Corrosion Reactions, J. Electroanal. Chem., 77, 1977, pp. 121-125.
U. Bertocci, AC Induced Corrosion. The Effect of an Alternating Voltage on Electrodes Under Charge-Transfer Control, Corrosion-Nace, vol. 35, No. 5, May 1979, pp. 211-215.

* cited by examiner

*Primary Examiner*—Timothy J Dole
*Assistant Examiner*—John Zhu
(74) *Attorney, Agent, or Firm*—Kermit D. Lopez; Luis M. Ortiz; Melissa Asfahani

(57) ABSTRACT

A method and apparatus for simultaneously and continuously monitoring both the general and localized corrosion of a working metallic electrode is provided, wherein a low frequency, low amplitude periodic potential excitation is used to perturb the electrode around its free corrosion potential. The potential is controlled with respect to a reference electrode by means of a potentiostat, and an auxiliary electrode used to stimulate current flow. The current response of the working electrode is monitored and analyzed continuously for general and localized corrosion activity. Means are provided for validation of the integrity of the current response to the applied potential excitation. Simultaneous and continuous outputs for both general and localized corrosion activity are also provided.

24 Claims, 4 Drawing Sheets

US 7,719,292 B2

METHOD AND APPARATUS FOR ELECTROCHEMICAL CORROSION MONITORING

FIELD OF THE INVENTION

The present invention relates generally to a method and apparatus for monitoring electrochemical corrosion, and in a particular though non-limiting embodiment, to a method and apparatus for monitoring the electrochemical corrosion of a working electrode.

BACKGROUND OF THE INVENTION

It is previously known that the corrosion of a metallic material can be studied using an electrochemical monitoring means such as Linear Polarization Resistance or Electrochemical Impedance. The theoretical basis for the use of electrochemical methods is usually founded in the Butler-Volmer relationship for a corroding material. The Butler-Volmer equation relates the current response of a system to an applied over-potential as a function of the corrosion current and the anodic and cathodic activation coefficients.

Another technique that has previously been used to study general corrosion processes is the Harmonic Distortion Analysis (HDA) method, which utilizes a low frequency sinusoidal voltage perturbation, and involves analysis of the current response in terms of the distortion due to the non-linearity of the current response. This technique involves further expansion of the Butler-Volmer equation, and facilitates analysis of the corrosion current, the anodic and cathodic activation coefficients and the so-called Stern-Geary constant.

While the above methods find wide usage for the study of general corrosion processes, those of skill in the appropriate arts have found that these techniques are generally unsuitable for the study of localized corrosion processes such as pitting corrosion.

For localized corrosion processes, a variety of other methods collectively termed "Electrochemical Noise" (EN) have been attempted. These techniques, which essentially involve analyzing the response of a corroding interface at the free corrosion potential with no applied perturbation, are used to evaluate the spontaneous changes in the corrosion processes, and are observed as current and potential fluctuations of a corroding specimen. Analysis of these potential and current noise signals may be in either the time or frequency domains.

During the measurement of low frequency impedance or when using the Harmonic Distortion technique, it is common practice to apply a high purity sine wave voltage perturbation and to measure the current at the fundamental frequency, and, in the case of Harmonic Distortion, to analyze the harmonic current content at integral multiples of the fundamental frequency. Since the applied voltage sinusoid is a periodic function, the current response at the fundamental frequency will be highly correlated with itself if the corrosion processes are stationary (in other words, when the processes do not change substantially during the period of measurements). Under these conditions, the self-correlation of the current response can be polled to validate the measurement, and also to serve as an indicator that further analysis (for example, harmonic distortion analysis) should be conducted to evaluate the corrosion processes for the anodic and cathodic activation coefficients. If, on the other hand, the corrosion processes are non-stationary, then the degree of self-correlation is substantially reduced, and will generally indicate a high probability for localized corrosion.

However, spontaneous changes occurring in the corrosion processes as a function of time can influence the current response to an applied potential perturbation, the extent of the influence depending on the relative magnitudes of the spontaneous variations in the corrosion potential, corrosion current and the activation coefficients. Thus, the stability of the response to an applied perturbation has often been viewed as a nuisance factor, with system and adventitious noise degrading the required response. Consequently, previously known electrochemical corrosion monitoring systems have been designed to reject noise, rather than analyze it in order to separate the deterministic response of the applied perturbation and any associated noise components.

There is, therefore, a longstanding and heretofore unmet need for an improved method and apparatus for continuously monitoring the corrosion of a working electrode, which provides simultaneous analysis for both the general corrosion and the localized corrosion processes, and which provides a reliable means for validation of the integrity of associated measurements.

SUMMARY OF THE INVENTION

A method of monitoring corrosion of a working electrode is provided, the method including: applying a low frequency, low amplitude, sinusoidal voltage perturbation signal to said working electrode; monitoring a current response returned from said working electrode; and analyzing said current response for periodic components in phase with said applied sinusoidal voltage perturbation signal and determining the degree of correlation of the signal with itself.

An apparatus for monitoring the corrosion of a working electrode is also provided, the apparatus including: a signal generator for supplying a low frequency, low amplitude, sinusoidal voltage perturbation signal to said working electrode; a monitor for monitoring a current response returned from said working electrode; and a current analyzer for analyzing said current response for periodic components in phase and 90° out of phase with said applied sinusoidal voltage perturbation signal, and for determining the degree of correlation of the signal with itself.

DETAILED DESCRIPTION

Figure 1:
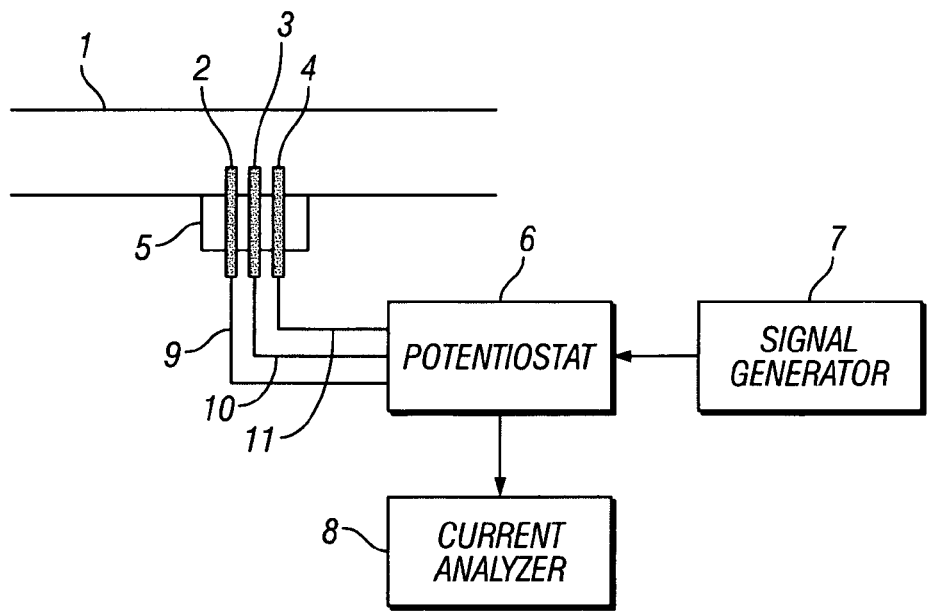
FIG. 1 is a schematic representation of a first example embodiment of the invention.

Referring now to the example embodiment depicted in FIG. 1, a pipeline 1 has an array of three electrodes 2, 3 and 4 representing a working electrode, a reference electrode and an auxiliary electrode, respectively. The electrodes are electrically isolated, from one another, and also from the pipeline 1, by means of a non-conducting seal 5.

The working electrode 2 comprises a metallic material of interest. The reference electrode 3 comprises, in one example, a calomel electrode. In other embodiments, reference electrode 3 instead comprises a pseudo-reference electrode fabricated from approximately the same material as the working electrode. In further embodiments, auxiliary electrode 4 comprises a chemically inert material (for example, platinum), which will not corrode substantially in the subject environment. In still further embodiments, auxiliary electrode 4 instead comprises approximately the same material as the working electrode.

In the depicted embodiment, the electrodes 2, 3 and 4 are connected by disposing a plurality of conductive members 9, 10 and 11 in electrical communication with a potentiostat 6. In a presently preferred embodiment, a signal generator 7 is used to supply a low frequency sinusoidal voltage to the working electrode via the potentiostat 6. The current flowing through the working electrode 2 can be analyzed using a current analyzer 8.

According to one example method, a low frequency sinusoidal potential perturbation is generated by signal generator 7 and applied by potentiostat 6 to working electrode 2, and then the signal representing the current response of the working electrode is monitored. The monitored signal is then analyzed using current analyzer 8 on a continuous basis over an integral number of periods of the sine wave, the method further including one or more of the following steps, which may be performed in any logical sequence or order:

(1) Analyzing the current for the total root mean square amplitude representative of the total response of the electrode;

(2) Analyzing the current to determine the mean or average component;

(3) Differentiating the current to remove the mean value;

(4) Integrating the differentiated current obtained in step 3 to reconstitute the original signal minus the mean value;

(5) Processing the output from step 4 to determine the autocorrelation function;

(6) Analyzing the output from step 4 to determine the root mean square amplitude;

(7) Analyzing the output from step 4 to determine the component in phase with the applied voltage sinusoidal perturbation;

(8) Analyzing the output from step 4 to determine the component 90° out of phase with the applied voltage sinusoidal perturbation;

(9) Using the outputs of steps 7 and 8 to calculate the modulus of the current;

(10) Determining whether the output from step 5 indicates a high degree of correlation, and if so, then analyzing the output from step 4 to determine harmonic components at twice and three times the applied frequency;

(11) Analyzing the output from step 7 to discern an indication of the general corrosion current of the working electrode according to the Linear Polarization Resistance method;

(12) Analyzing the outputs from steps 7 and 10 to discern an indication of the general corrosion current according to the Harmonic Distortion Analysis method;

(13) Analyzing the outputs from steps 7 and 10 according to the Harmonic Distortion Analysis method to determine values for the anodic and cathodic activation coefficients and the Stern-Geary constant;

(14) Examining the output from step 5 to discern an indication of the propensity of the corrosion processes to general or localized corrosion. If the value is close to 1, then the corrosion processes are deemed to be general; if the value approaches 0, the corrosion processes are deemed localized;

(15) Analyzing the difference between outputs from steps 6 and 9 to discern an indication of the localized corrosion processes;

(16) Analyzing the ratio of the output from step 15 to the output of step 9 to discern an indication of the propensity for localized corrosion;

(17) Comparing the output from steps 1 and 6 to discern an indication of stable pitting or crevice corrosion.

In one example embodiment, the electrode system 2-4 comprises a working electrode 2, a saturated calomel electrode (SCE) which functions as a reference electrode 3, and an insert type auxiliary electrode 4. In this arrangement, the potential of the working electrode 2 is maintained at an observed free corrosion potential by means of a DC bias present in the system. A low frequency sine wave potential perturbation is applied so as to polarize the working electrode 2 around the free corrosion potential. The current response is then monitored and analyzed according to the steps above.

Using the same basic arrangement of electrodes, the above method can be used for evaluating the current response at potentials substantially removed from the free corrosion potential by means of application of a DC bias, for example, for evaluation of the propensity of a material to pitting corrosion using anodic polarization.

In another example embodiment, three identical electrodes are used for the working, reference and auxiliary electrodes. Such an arrangement is more convenient for monitoring systems where a reference electrode such as the SCE may be prone to deterioration, for example, as in operating pipelines and plants. In addition, since all three electrodes are basically identical, the necessity for the application of a DC bias is avoided.

In a further embodiment, two identical electrodes are used, one serving as the working electrode 2, with the other serving as a combined reference and auxiliary electrode 3-4. In a variation of this embodiment, working electrode 2 is substantially smaller in area (e.g., <10%) than the combined auxiliary/reference electrode 3-4 in order to better facilitate the analysis described above.

In a still further embodiment (for example, as would be especially suitable for an operating pipeline or plant), the probe comprises a single working electrode 2 formed of the same material as the pipeline or plant, and the plant itself is used as the combined reference/auxiliary electrode 3-4.

Figure 2:
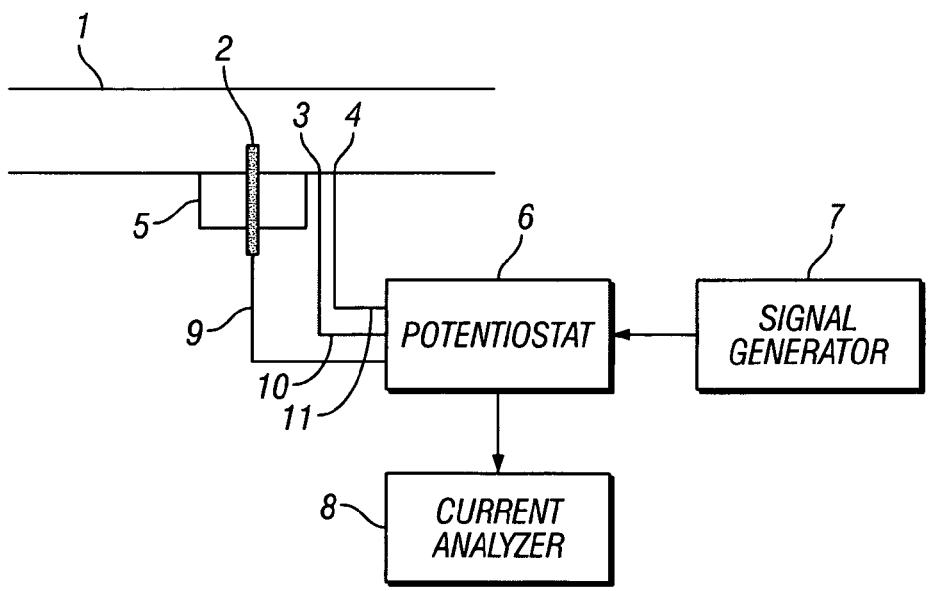
FIG. 2 is a schematic representation of a second example embodiment of the invention.

Referring now to FIG. 2, another example embodiment is depicted, in which the numbering scheme used in FIG. 1 is maintained for clarity. This arrangement differs from the embodiment depicted in FIG. 1 in that it comprises only a single electrode 2 (the working electrode) inserted into the pipeline. The pipeline itself acts as a combined reference and auxiliary electrode, which has a substantially greater surface area than the working electrode. Thus, the response of the system is governed by the smaller of the electrodes (the working electrode).

The electrodes are disposed in electrical communication with potentiostat 6 by means of conducting members 9, 10 and 11, which can simply be wires or any other type of electrical communication member suitable for the functions described herein. A signal generator 7 applies a low frequency sinusoidal voltage to the working electrode via the potentiostat 6, and the current flowing through the working electrode is analyzed using the current analyzer 8 in a manner consistent with the analysis method outlined above.

In the embodiments depicted in FIGS. 1 and 2, separate signal generators, potentiostats and current analyzers are depicted. Those of ordinary skill in the art, however, will readily appreciate that in practice, these components could be incorporated into a single device or composite device coupled with a computer or logic system that will perform the waveform generation, voltage and current monitoring, and digital signal processing techniques required to provide the outputs described above.

Figure 3:
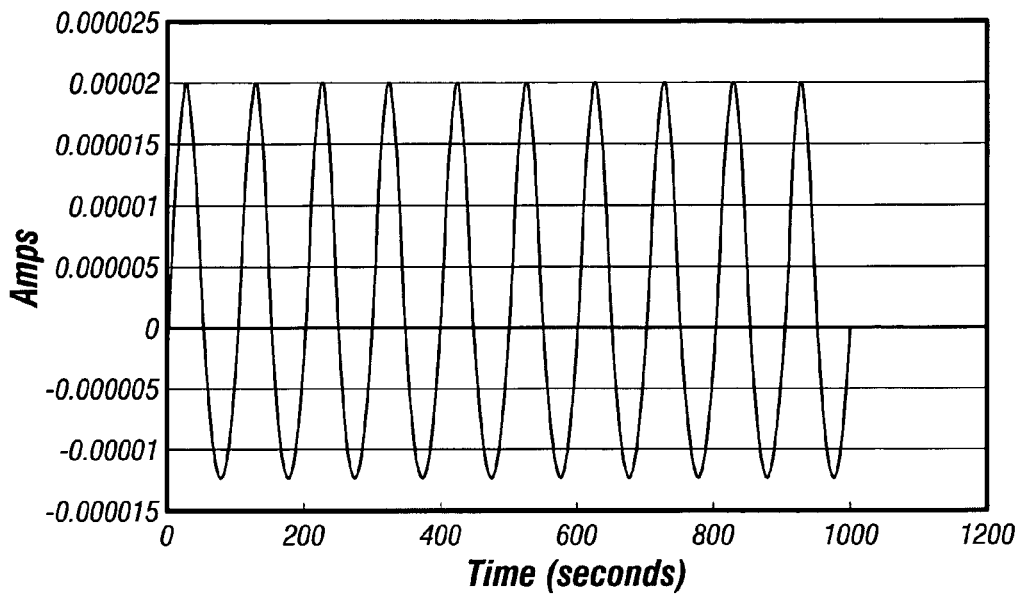
FIG. 3 is a graphical representation of the current response of a corroding electrode with only a small amount of electrochemical noise, representing principally general corrosion.

FIG. 3 illustrates the current response as a function of time of a working electrode having a low rate of general corrosion perturbed by a low amplitude, low voltage sinuoisoid at a frequency of around 0.01 Hz.

Figure 4:
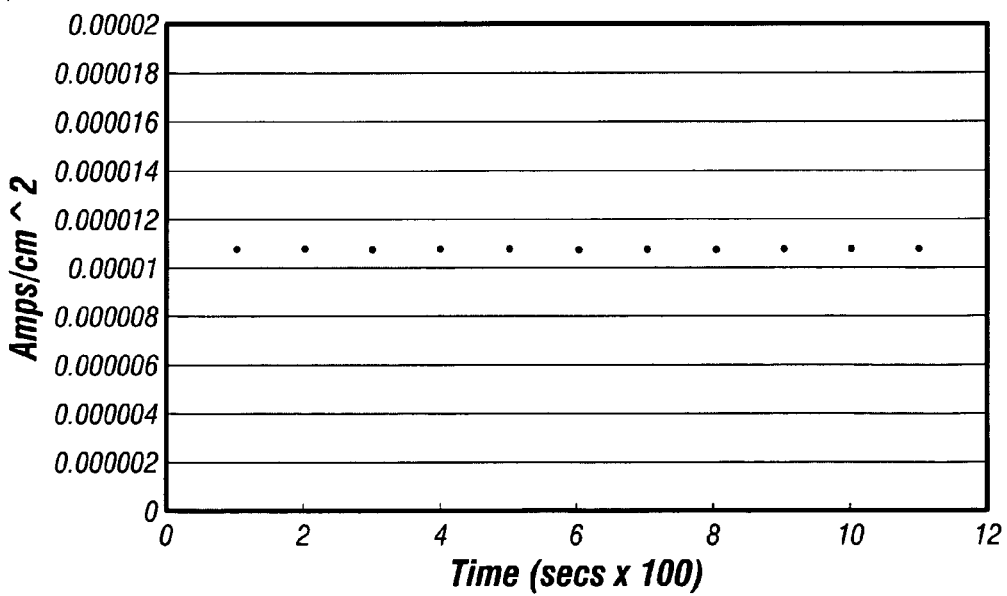
FIG. 4 is a graphical representation of the continuous output of the general corrosion current depicted in FIG. 3, further considered as a function of time.

FIG. 4 illustrates the analyzed output of the signal illustrated in FIG. 3 in terms of the general corrosion current density as a function of time over successive integral periods of the sine wave.

Figure 5:
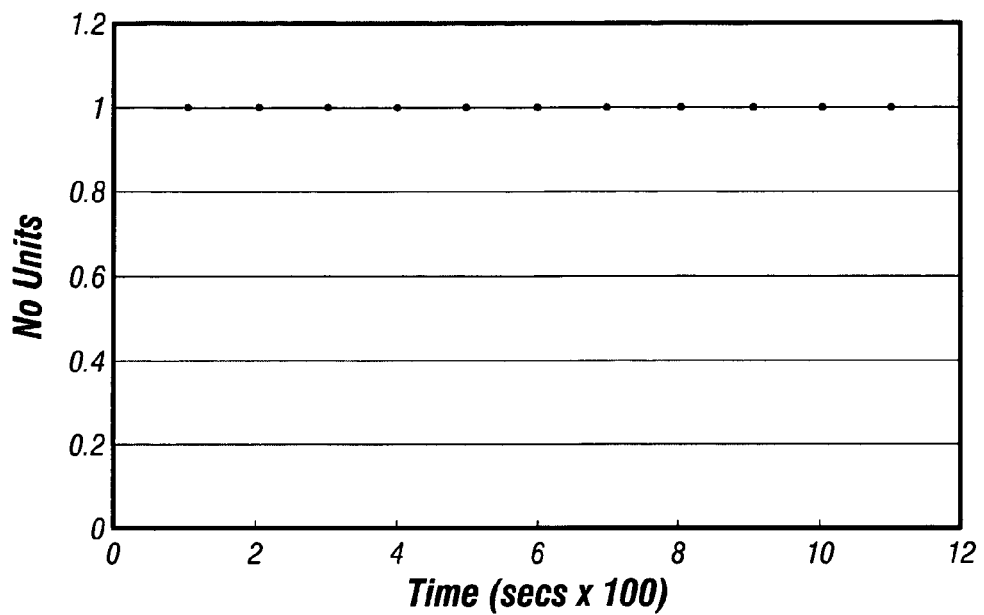
FIG. 5 is a graphical representation of the current correlation function derived from the general corrosion depicted in FIG. 3.

FIG. 5 illustrates the analyzed output of the signal illustrated in FIG. 3 in terms of the autocorrelation function, the values of which are very close to 1, indicating that the processes are stationary during the measurement process.

Figure 6:
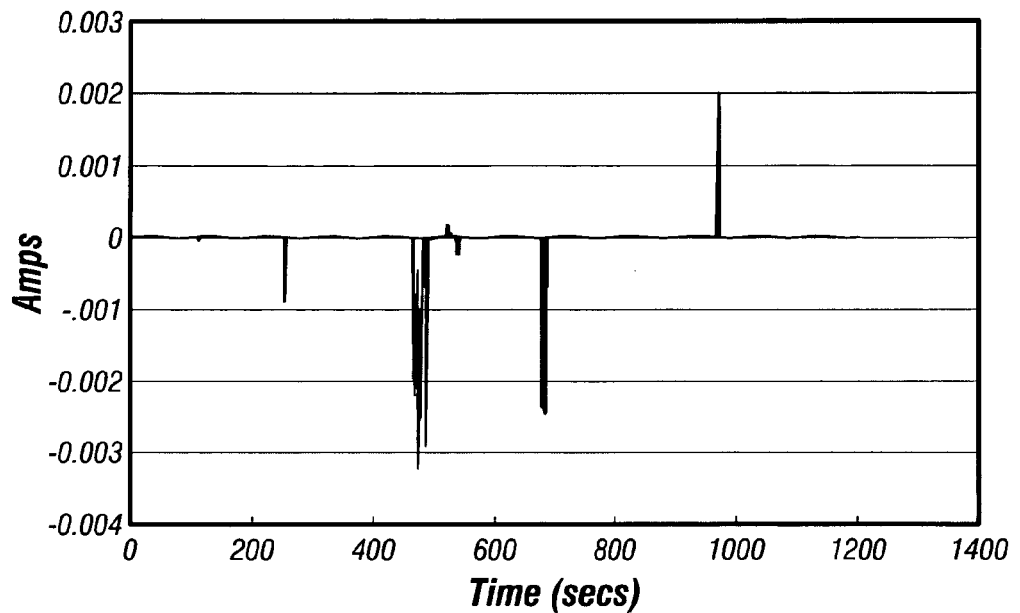
FIG. 6 is a graphical representation of the current response of a corroding electrode associated with substantial electrochemical noise.

FIG. 6 illustrates the current response as a function of time of a working electrode having a low rate of general corrosion, similar to that in FIG. 3, but having random noise signals representative of localized corrosion events.

Figure 7:
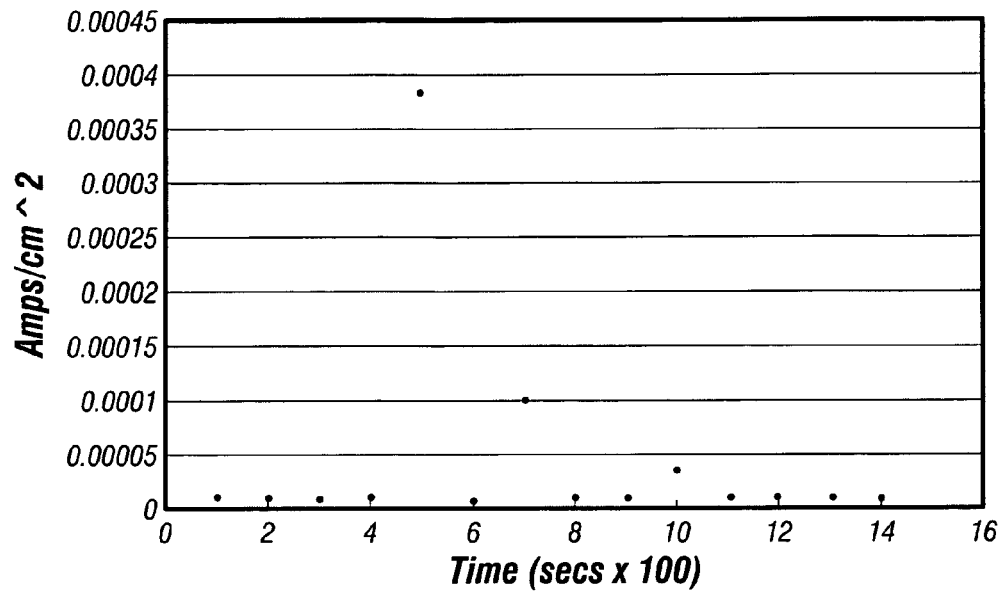
FIG. 7 is a graphical representation of the continuous output of the general corrosion parameters obtained from the example embodiment depicted in FIG. 6.

FIG. 7 illustrates the analyzed output of the signal illustrated in FIG. 6 in terms of the general corrosion current density as a function of time, which is indicative of instability in the corrosion processes.

Figure 8:
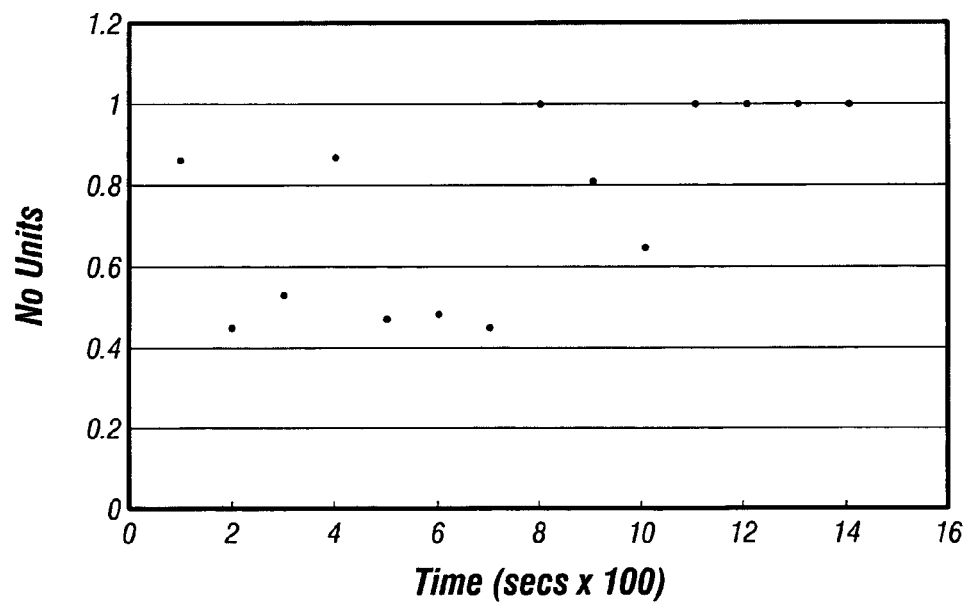
FIG. 8 is a graphical representation of the current correlation function obtained from the example embodiment depicted in FIG. 6. Note that the localized corrosion events result in substantial shifts in the autocorrelation function.

FIG. 8 illustrates the analyzed output of the signal illustrated in FIG. 6 in terms of the autocorrelation function. Comparing FIG. 8 to FIG. 5 (for the general corrosion example), it is apparent that the autocorrelation function deviates significantly from the value of 1 during the periods of random corrosion activity, indicating that the corrosion processes are localized during these periods.

The above figures are representative, though certainly not exhaustive, of the types of outputs that can be obtained from the analysis steps described. Any, or indeed all, of the outputs may be selected in order to obtain data of relevance in a particular operational environment.

The foregoing specification is provided for illustrative purposes only, and is not intended to describe all possible aspects of the present invention. Moreover, while the invention has been shown and described in detail with respect to several exemplary embodiments, those of ordinary skill in the pertinent arts will appreciate that minor changes to the description, and various other modifications, omissions and additions may also be made without departing from either the spirit or scope thereof.

The invention claimed is:

1. A method of monitoring corrosion of a working electrode, said method comprising:
    applying a low frequency, low amplitude, sinusoidal voltage perturbation signal to said working electrode;
    monitoring a current response returned from said working electrodes said current response including a current signal;
    analyzing said current response for periodic components in-phase and 90° out-of-phase with said sinusoidal voltage perturbation signal;
    determining a degree of correlation of said current signal with itself, wherein said sinusoidal voltage perturbation signal is continuously applied and analyzed to provide a continuous output of general corrosion and said degree of correlation; and
    indicating a propensity for localized corrosion by a ratio of a difference between a total observed current response of said working electrode and a modulus of said current response of said working electrode divided by the modulus of said current response of said working electrode.

2. The method of monitoring corrosion of a working electrode of claim 1, wherein said general corrosion of said working electrode is indicated by the amplitude of the in-phase sinusoidal components of said current response, and a propensity for localized corrosion by said degree of correlation of said current response with itself.

3. The method of monitoring corrosion of a working electrode of claim 1, wherein a difference between a total root mean square of said current response and a modulus of said current response is related to said propensity for localized corrosion on said working electrode.

4. The method of monitoring corrosion of a working electrode of claim 1, wherein said degree of correlation of said current signal with itself is used to validate further analysis of said current signal in terms of higher harmonic components at integral multiples of said sinusoidal voltage perturbation signal for deriving a further corrosion rate from a harmonic distortion analysis.

5. The method of monitoring corrosion of a working electrode of claim 1, wherein an anodic activation coefficient, a cathodic activation coefficient, and a Stern-Geary constant are also computed.

6. The method of monitoring corrosion of a working electrode of 1, wherein said sinusoidal voltage perturbation signal is continuously applied and analyzed to provide continuous outputs of said corrosion rate, said anodic activation coefficient, said cathodic activation coefficient, and said Stern-Geary constant.

7. The method of monitoring corrosion of a working electrode of claim 1, wherein said total observed current response of said working electrode is calculated using said current response of said working electrode minus a mean value to determine the root mean square amplitude.

8. The method of monitoring corrosion of a working electrode of claim 1, wherein said modulus of said original current response of said working electrode is calculated using said current response of said working electrode to determine a component in-phase with said applied sinusoidal voltage perturbation signal, and a component 90° out-of-phase with said applied sinusoidal voltage perturbation signal.

9. An apparatus for monitoring the corrosion of a working electrode, said apparatus comprising:
    a signal generator for supplying a low frequency, low amplitude, sinusoidal voltage perturbation signal to said working electrode;
    a monitor for monitoring a current response returned from said working electrode, said current response including a current signal; and
    a current analyzer for analyzing said current response for periodic components in-phase with applied said sinusoidal voltage perturbation signal, and for determining a degree of correlation of said current signal with itself; and means for indicating a propensity for localized corrosion by comparing a ratio of a difference between a total observed current response of said working electrode and a modulus of said current response of said working electrode divided by the modulus of said current response of said working electrode.

10. The apparatus for monitoring corrosion of a working electrode of claim 9, further comprising means for indicating when general corrosion of said working electrode is indicated by an amplitude of the in-phase sinusoidal components of said current signal, and said propensity for localized corrosion by said degree of correlation of said current response with itself.

11. The apparatus for monitoring corrosion of a working electrode of claim 9, further comprising means for indicating when a difference between a total root mean square of a modulus of current response is related to said propensity for localized corrosion on said working electrode.

12. The apparatus for monitoring corrosion of a working electrode of claim 9, further comprising means for continuously applying said sinusoidal voltage perturbation signal, and means for analyzing a return signal obtained from said working electrode to provide a continuous output to determine a propensity for general corrosion and to determine said degree of correlation.

13. The apparatus for monitoring corrosion of a working electrode of claim 9, further comprising means for validating further analysis of said current response in terms of higher harmonic components at integral multiples of said sinusoidal voltage perturbation signal for deriving a further corrosion rate from a harmonic distortion analysis using said degree of correlation of said current response with itself.

14. The apparatus for monitoring corrosion of a working electrode of claim 13, further comprising means for continuously applying said sinusoidal voltage perturbation signal, and means for analyzing a return signal obtained from said working electrode to provide a continuous output for determining said propensity for localized corrosion.

15. The apparatus for monitoring corrosion of a working electrode of claim 13, further comprising means for computing an anodic activation coefficient, a cathodic activation coefficients, and a Stern-Geary constant.

16. The apparatus for monitoring corrosion of a working electrode of claim 13, further comprising means for continuously applying said sinusoidal voltage perturbation signal, and means for analyzing a return signal obtained from said working electrode to provide continuous outputs to determine said corrosion rate.

17. The apparatus for monitoring corrosion of a working electrode of 13, further comprising means for continuously applying said sinusoidal voltage perturbation signal, and means for analyzing a return signal obtained from said working electrode to provide continuous outputs of said anodic activation coefficient, said cathodic activation coefficient, and said Stern-Geary constant.

18. The apparatus for monitoring corrosion of a working electrode of claim 9, further comprising means for computing the ratio of the difference between a total current response of said working electrode and has been changed to the modulus of the current response of said working electrode to a general corrosion current of said working electrode to determine the propensity for localized corrosion.

19. The apparatus for monitoring corrosion of a working electrode of claim 18, wherein said total observed current response of said working electrode is calculated using said current response of said working electrode minus a mean value to determine the root mean square amplitude.

20. The apparatus for monitoring corrosion of a working electrode of claim 18, wherein said modulus of the current response of said working electrode is calculated using said current response of said working electrode to determine a component in-phase with said applied sinusoidal voltage perturbation signal, and a component 90° out-of-phase with said applied sinusoidal voltage perturbation signal.

21. The apparatus for monitoring corrosion of a working electrode of claim 18, wherein said general corrosion current of said working electrode is calculated using said current response of said working electrode minus a mean value to determine a component in-phase with an applied sinusoidal perturbation, and to analyze said current response of said working electrode according to linear polarization resistance.

22. The apparatus for monitoring corrosion of a working electrode of claim 18, wherein said general corrosion current of the working electrode is calculated using said current response of said working electrode minus a mean value to determine a component in-phase with an applied sinusoidal perturbation, and to analyze self-correlation of said current response of said working electrode, according to harmonic distortion analysis.

23. The apparatus for monitoring corrosion of a working electrode of claim 9, wherein said total observed current response of said working electrode is calculated using said current response of said working electrode minus a mean value to determine the root mean square amplitude.

24. The apparatus for monitoring corrosion of a working electrode of claim 9, wherein said modulus of the current response of said working electrode is calculated using said original current response of said working electrode to determine a component in-phase with said applied sinusoidal voltage perturbation signal, and a component 90° out-of-phase with said applied sinusoidal voltage perturbation signal.

* * * * *